(12) United States Patent
Lubisch et al.

(10) Patent No.: US 7,041,675 B2
(45) Date of Patent: May 9, 2006

(54) HETEROCYCLIC COMPOUNDS AND THEIR USE AS PARP INHIBITORS

(75) Inventors: Wilfried Lubisch, Heidelberg (DE); Michael Kock, Schifferstadt (DE); Thomas Hoeger, Edingen-Neckarhausen (DE); Roland Grandel, Dossenheim (DE); Reinhold Mueller, Schifferstadt (DE); Sabine Schult, Speyer (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 10/182,532

(22) PCT Filed: Jan. 25, 2001

(86) PCT No.: PCT/EP01/00790

§ 371 (c)(1),
(2), (4) Date: Nov. 18, 2002

(87) PCT Pub. No.: WO01/57038

PCT Pub. Date: Aug. 9, 2001

(65) Prior Publication Data

US 2003/0134843 A1    Jul. 17, 2003

(30) Foreign Application Priority Data

Feb. 1, 2000   (DE) ................... 100 04 238

(51) Int. Cl.
*A61K 31/437* (2006.01)
*A61K 31/4709* (2006.01)
*A61K 31/4725* (2006.01)
*A61P 9/10* (2006.01)
*C07D 471/04* (2006.01)

(52) U.S. Cl. ............ 514/300; 514/303; 514/299; 514/217.07; 514/217.04; 514/259; 514/249; 514/253.04; 514/233.2; 514/218; 540/572; 540/597; 544/127; 544/362; 544/284; 544/353; 546/121; 546/120; 546/112

(58) Field of Classification Search ........... 546/121, 546/120, 112; 540/572, 597; 544/127, 362, 544/284, 353; 514/300, 303, 299, 218, 217.04, 514/259, 253.04, 233.2, 249
See application file for complete search history.

(56) References Cited

U.S. PATENT DOCUMENTS 4,096,145 A    6/1978   Schefczik

FOREIGN PATENT DOCUMENTS

| BE | 620141 | 10/1962 |
|----|--------|---------|
| DE | 2025427 | 12/1971 |
| WO | WO 97/04771 | 2/1997 |
| WO | WO 99/64572 | 12/1999 |
| ZA | 85/1335 | 2/1985 |

OTHER PUBLICATIONS

Zhang J, (1999) Emerging Drugs: The Prospect for improved Medicines. Ashley Publications Ltd. pp. 209-221.*
Zhang J and Li JH. (2000) Cell Death, Szabo C (ed.) CRC Press, Boca, Raton. pp. 279-304).*
J. Reisch et al., J. Heterocycl. Chem. 1990, 27, 287-289.
V. Burkart et al., Nature Med. 1999, 5, 314-319.
S. Cuzzocrea et al., Eur. J. Pharmacol. 1998, 342, 67-76.
S. Cuzzocrea et al., Br. J. Pharmacol. 1997, 121, 1065-1074.
G. Chen et al., Cancer Chemo. Pharmacol. 1988 22, 303-307.
W. Ehrlich et al., Rheumatol. Int. 1995, 15, 171-172.
K. Ikai et al., J. Histochem. Cytochem. 1983, 31, 1261-1264.

(Continued)

*Primary Examiner*—Evelyn Mei Huang
(74) *Attorney, Agent, or Firm*—Wood, Phillips, Katz Clark & Mortimer

(57) ABSTRACT

The invention relates to compounds of the formula I

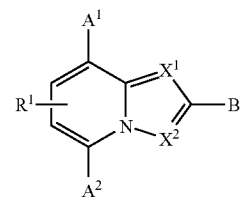

and the tautomeric forms, possible enantiomeric and diastereomeric forms thereof, and prodrugs thereof, and use thereof as PARP inhibitors.

6 Claims, No Drawings

OTHER PUBLICATIONS

S. Shall, Adv. Radiat. Biol. 1984, 11, 1-69.
M.S. Satoh et al., Nature 1992, 356, 356-358.
H. Kroger et al., Inflammation 1996, 20, 203-215.
C. Thiemermann et al., Proc. Natl. Acad. Sci. USA 1997, 94, 679-683.
D. Weltin et al., Int. J. Immunopharmacol. 1995, 17, 265-271.
C. Szabo et al., Proc. Natl. Acad. Sci. USA 1998, 95, 3867-3872.
O.K. Kim et al., Bioorg. Med Chem Lett. 1997, 7, 2753-2758.
Buu-Hoi et al., Bull. Soc. Chim Fr. 1961, 1344.
Y. Abe et al., J. Med. Chem. 1998, 41, 564-578.
L. Fisher et al., J. Med. Chem. 1972, 15, 982-985.
Teulade et al., Eur. J. Med. Chem. Chim. Therap. 1979, 13, 271-276.

* cited by examiner

HETEROCYCLIC COMPOUNDS AND THEIR USE AS PARP INHIBITORS

CROSS-REFERENCE TO RELATED APPLICATION

This application is a Section 371 application of PCT/EP01/00790 filed Jan. 25, 2000.

The present invention relates to novel heterocyclic compounds, the preparation thereof and the use as inhibitors of the enzyme poly(ADP-ribose)polymerase or PARP (EC 2.4.2.30) for producing drugs.

Poly(ADP-ribose)polymerase (PARP) or, as it is also called, poly(ADP-ribose) synthase (PARS) is a regulatory enzyme which is found in cell nuclei (K. Ikai et al., J. Histochem. Cytochem. 1983, 31, 1261–1264). It is assumed that PARP plays a part in the repair of DNA breaks (M. S. Satoh et al., Nature 1992, 356, 356–358). Damage or breaks in DNA strands activate the enzyme PARP which, when it is activated, catalyzes the transfer of ADP-ribose from NDA (S. Shaw, Adv. Radiat. Biol., 1984, 11, 1–69). Nicotinamide is released from NAD during this. Nicotinamide is converted back into NAD by other enzymes with consumption of the energy carrier ATP. Overactivation of PARP would accordingly result in a nonphysiologically high consumption of ATP, and this leads, in the extreme case, to cell damage and cell death.

It is known that free radicals such as superoxide anion, NO and hydrogen peroxide may lead to DNA damage in cells and thus activate PARP. The formation of large amounts of free radicals is observed in a number of pathophysiological states, and it is assumed that this accumulation of free radicals leads or contributes to the observed cellular and organ damage. This includes, for example, ischemic states of organs such as in stroke, myocardial infarct (C. Thiemermann et al., Proc. Natl. Acad. Sci. USA, 1997, 94, 679–683) or ischemia of the kidneys, but also after reperfusion damage as occurs, for example, after the lysis of myoccardial infarct (see above: C. Thiemermann et al.). Inhibition of the enzyme PARP might accordingly be a means of preventing or alleviating this damage at least in part. PARP inhibitors might thus represent a novel therapeutic principle for treating a number of disorders.

The enzyme PARP influences the repair of DNA damage and might thus also play a part in the therapy of cancers because a greater action potential on tumor tissue was observed (G. Chen et al. Cancer Chemo. Pharmacol. 1988, 22, 303) in combination with substances with cytostatic activity. Nonlimiting examples of tumors are leukemia, glioblastomas, lymphomas, melanomas and carcinomas of the breast and cervix.

It has additionally been found that PARP inhibitors may show an immunosuppressant effect (D. Weltin et al. Int. J. Immunopharmacol. 1995, 17, 265–271).

It has likewise been discovered that PARP is involved in immunological disorders and diseases in which the immune system plays an important part, such as, for example, rheumatoid arthritis and septic shock, and that PARP inhibitors may have a beneficial effect on the course of the disorder (H. Kröger et al. Inflammation 1996, 20, 203–215; W. Ehrlich et al. Rheumatol. Int. 1995, 15, 171–172; C. Szabo et al., Proc. Natl. Acad. Sci. USA 1998, 95, 3867–3872; S. Cuzzocrea et al. Eur. J. Pharmacol. 1998, 342, 67–76).

The PARP inhibitor 3-aminobenzamide has furthermore shown protective effects in a model of circulatory shock (S. Cuzzocrea et al., Br. J. Pharmacol. 1997, 121, 1065–1074).

There is likewise experimental evidence that inhibitors of the enzyme PARP might be useful as agents for treating Diabetes mellitus (V. Burkart et al. Nature Med. 1999, 5, 314–319).

PARP means for the purpose of the invention also isoenzymes of the PARP enzyme described above. Examples of such isoenzymes are PARP II and PARP III, as described in WO99/64572.

Imidazopyridines and derivatives of this bicyclic compound represent a chemical class which has been widely used in organic synthesis. Likewise, derivatives in which an imidazopyridine carries a carboxamide group on the 6-membered ring have already been described. In DE 2025427, DE 2611665, J. Reisch et al., J. Heterocycl. Chem. 1990, 27, 287–189 and Y. Abe et al., J. Med. Chem. 1998, 41, 564–578, imidazopyridines having carboxamide groups in position 4 but being further substituted on the carboxamide nitrogen atom, and being either unsubstituted or substituted only with simple radicals such as methyl in position 2, were prepared.

Few imidazopyridines having a carboxamide group in position 7 are known. There has merely been preparation of 1-nitro-imidazo[1,2-a]pyridine-7-carboxamide in Teulade et al. Eur. J. Med. Chem. Chim. Therap. 1979, 13, 271.

Imidazopyridines having a carboxamide group in position 6 and position 5 have already been described several times. Thus, derivatives with aromatic rings in position 2 are also known in this case. These compounds and further derivatives were described in L. Fisher et al. J. Med. Chem. 1972, 15, 982, Buu-Hoi et al. Bull. Soc. Chim Fr. 1961, 1344, and O. K. Kim et al. Bioorg. Med. Chem. Lett. 1997, 7, 27. Buu-Hoi (see above) and BE 620141 described 2-phenyl-imidazo[1,2-a]pyridines having a carboxamide group in position 6 or 7. However, in none of the references cited above is there to be found a reference to the possibility of such compounds being used in therapy owing to these compounds inhibiting enzymes such as PARP.

It has further been found, surprisingly, that heterocyclic compounds such as, for example, imidazopyridine derivatives are very effective inhibitors of the enzyme PARP. It has additionally been found that the novel imidazo[1,2-a]pyridine derivatives having a primary carboxamide group in position 4 or 8 show good inhibitory activity on the enzyme PARP by comparison with the positional isomers having a carboxamide group in position 6 or 7, for example in Buu-Hoi (see above) and in BE 620141, whereas the positional isomers have only very poor activity or none at all.

Novel heterocyclic compounds of the general formula I which are potent PARP inhibitors are described in the present invention.

The present invention relates to heterocyclic compounds of the general formula I

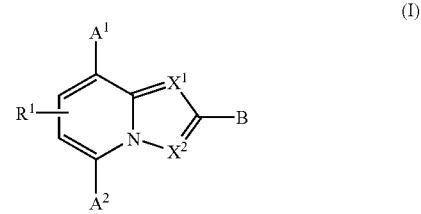

(I)

in which either $A^1$ or $A^2$
is $CONH_2$, and the other radical $A^2$ or $A^1$ in each case is hydrogen, chlorine, fluorine, bromine, iodine, $C_1$–$C_6$-alkyl, OH, nitro, $CF_3$, CN, $NR^{11}R^{12}$, NH—CO—$R^{13}$, O—$C_1$–$C_4$-alkyl, and $X^1$ can be N and C—$R^2$, and $X^2$ can be, independently of $X^1$, N and C—$R^2$, and $R^2$ is hydrogen, $C_1$–$C_6$-alkyl, $C_1$–$C_4$-alkyl-phenyl, phenyl and $R^1$ is hydrogen, chlorine, fluorine, bromine, iodine, $C_1$–$C_6$-alkyl, OH, nitro, $CF_3$, CN, $NR^{11}R^{12}$, NH—CO—$R^{13}$, O—$C_1$–$C_4$-alkyl, where $R^{11}$ and $R^{12}$ are, independently of one another, hydrogen or $C_1$–$C_4$-alkyl, and $R^{13}$ is hydrogen, $C_1$–$C_4$-alkyl, $C_1$–$C_4$-alkyl-phenyl or phenyl, and B can be an unsaturated, saturated or partially unsaturated mono-, bi- or tricyclic ring with a maximum of 15 carbon atoms, such as, for example, phenyl, naphthalene, tetrahydronaphthalene, indane, carbazole, fluorine, cyclohexane, an unsaturated, saturated or partially unsaturated mono-, bi- or tricyclic ring with a maximum of 14 carbon atoms and 0 to 5 nitrogen atoms, 0 to 2 oxygen atoms and 0 to 2 sulfur atoms, such as, for example, pyridine, thiophene, quinoline, quinoxaline, furan, imidazole, pyrrole, indole, benzimidazole, pyrimidine, pyrazine, benzofuran, benzothiophene and isoxazole, each of which may also be substituted by one $R^4$ and a maximum of 3 identical or different $R^5$ radicals, and $R^4$ is hydrogen and $-(D)_p-(E)_s-(F^1)_q-G^1-(F^2)_r-(G^2)-G^3$, where D is S, $NR^{43}$ and O E phenyl,

—$SO_2$—, —$SO_2NH$—, —NHCO—, —CONH, —$NHSO_2$—, and s is 0 and 1 and $G^1$ is a bond or can be an unsaturated, saturated or partially unsaturated mono-, bi- or tricyclic ring with a maximum of 15 carbon atoms, an unsaturated, saturated or partially unsaturated mono-, bi- or tricyclic ring with a maximum of 14 carbon atoms and 0 to 5 nitrogen atoms, 0 to 2 oxygen atoms and 0 to 2 sulfur atoms, each of which is also substituted by a maximum of 3 different or identical $R^5$ radicals, and one or two carbon or sulfur atoms may also carry one or two =O groups, and $G^2$ is $NR^{41}R^{42}$ and

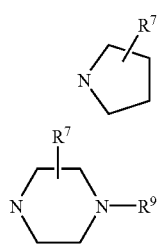
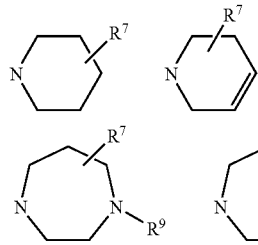
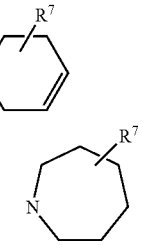

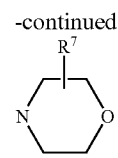

or is a bond and $G^3$ can be an unsaturated, saturated or partially unsaturated mono-, bi- or tricyclic ring with a maximum of 15 carbon atoms, an unsaturated, saturated or partially unsaturated mono-, bi- or tricyclic ring with a maximum of 14 carbon atoms and 0 to 5 nitrogen atoms, 0 to 2 oxygen atoms and 0 to 2 sulfur atoms, each of which is also substituted by a maximum of 3 different or identical $R^5$ radicals, and one or two carbon or sulfur atoms may also carry one or two =O groups, or is hydrogen, and p can be 0 and 1 and $F^1$ can be a $C_1$–$C_8$-alkyl chain, and $F^2$ independently of $F^1$ has the same meaning as $F^1$, q can be 0 and 1, and r can be 0 and 1 and $R^{41}$ can be hydrogen, $C_1$–$C_6$-alkyl, $C_1$–$C_6$-alkyl-phenyl, phenyl, it being possible for each carbon atom of the alkyl chains and the phenyl rings also to carry a maximum of two $R^6$ radicals, and $(CH_2)_t$—K and $R^{42}$ can be hydrogen, $C_1$–$C_6$-alkyl, —$CO_2$—$R^8$, —CO—$R^8$, —$SO_2$—$R^8$, —(C=NH)—$R^8$ and —(C=NH)—$NHR^8$ and $R^{43}$ can be hydrogen and $C_1$–$C_4$-alkyl and t can be 1,2,3,4 and K can be $NR^{11}R^{12}$, $NR^{11}$—$C_1$–$C_4$-alkyl-phenyl, pyrrolidine, piperidine, 1,2,5,6-tetrahydropyridine, morpholine, homopiperidine, homopiperazine, piperazine, each of which can also be substituted by a $C_1$–$C_6$-alkyl radical or also by a $C_1$–$C_6$-alkyl-phenyl radical and the phenyl radical can also be substituted by a maximum of two $R^{81}$, and $R^5$ can be hydrogen, chlorine, fluorine, bromine, iodine, $C_1$–$C_6$-alkyl, OH, nitro, $CF_3$, CN, $NR^{11}R^{12}$, NH—CO—$R^{13}$, O—$C_1$–$C_4$-alkyl $R^6$ can be hydrogen, chlorine, fluorine, bromine, iodine, $C_1$–$C_6$-alkyl, OH, nitro, $CF_3$, CN, $NR^{11}R^{12}$, NH—CO—$R^{13}$, O—$C_1$–$C_4$-alkyl $R^7$ can be hydrogen, $C_1$–$C_6$-alkyl, phenyl, it being possible for the ring also to be substituted by up to two identical or different $R^{71}$ radicals, and an amine $NR^{11}R^{12}$ or a cyclic saturated amine with 3 to 7 members, which may also be substituted by an alkyl radical $C_1$–$C_6$-alkyl, it being possible for the radicals $R^{11}$, $R^{12}$ and $R^{13}$ in K, $R^5$, $R^6$ and $R^7$ independently of one another to assume the same meaning as in $R^1$, and $R^{71}$ can be OH, $C_1$–$C_6$-alkyl, O—$C_1$–$C_4$-alkyl, chlorine, bromine, iodine, fluorine, $CF_3$, nitro, $NH_2$, and $R^8$ can be $C_1$–$C_6$-alkyl, $CF_3$, phenyl, $C_1$–$C_4$-alkyl-phenyl, it being possible for the ring also to be substituted by up to two $R^{81}$ radicals, and $R^{81}$ can be OH, $C_1$–$C_6$-alkyl, O—$C_1$–$C_4$-alkyl, chlorine, bromine, iodine, fluorine, $CF_3$, nitro, $NH_2$, and $R^9$ can be hydrogen, $C_1$–$C_6$-alkyl, $C_1$–$C_4$-alkyl-phenyl, $CO_2$—$C_1$–$C_4$-alkyl-phenyl, $CO_2$—$C_1$–$C_4$-alkyl, —$SO_2$-phenyl, —$COR^8$ and phenyl, it being possible for the phenyl rings also to be substituted by up to two identical or different $R^{91}$ radicals, and $R^{91}$ can be OH, $C_1$–$C_6$-alkyl, O—$C_1$–$C_4$-alkyl, chlorine, bromine, iodine, fluorine, $CF_3$, nitro and $NH_2$, and the tautomeric forms, possible enantiomeric and diasteromeric forms thereof, and prodrugs thereof.

The radicals e.g. $R^5$, $R^{11}$, $R^{12}$ and $R^{13}$ may assume the various meanings independently of one another and independently of the respective meaning of another radical (for example $A^1$, $R^1$, $R^5$ etc).

$C_x$–$C_y$-Alkyl always means, where possible, branched and unbranched $C_x$–$C_y$-alkyl. Unbranched alkyl is preferred.

Preferred compounds of the formula I are those where $X^1$ is an N atom, and $X^2$ is CH, and $R^1$ is hydrogen, and $A^1$ is $CONH_2$, and $A^2$ is hydrogen, and all the other variables have the above meaning.

Particularly preferred compounds of the formula I are those where $X^1$ is an N atom, and $X^2$ is CH, and $R^1$ is hydrogen, and $A^1$ is $CONH_2$, and $A^2$ is hydrogen, and B is phenyl, pyridine or piperidine, each of which may also be substituted by an $R^4$ and $R^5$ radical, and all the other variables have the above meaning.

The compounds of the formula I can be employed as racemates, as enantiopure compounds or as diastereomers. If enantiopure compounds are desired, these can be obtained, for example, by carrying out a classical racemate resolution with the compounds of the formula I or their intermediates using a suitable optically active base or acid.

The invention also relates to compounds which are mesomers or tautomers of compounds of the formula I.

The invention further relates to the physiologically tolerated salts of the compounds I which can be obtained by reacting compounds I with a suitable acid or base. Suitable acids and bases are listed, for example, in Fortschritte der Arzneimittelforschung, 1966, Birkhäuser Verlag, Vol. 10, pp. 224–285. These include, for example, hydrochloric acid, citric acid, tartaric acid, lactic acid, phosphoric acid, methanesulfonic acid, acetic acid, formic acid, maleic acid, fumaric acid etc, or sodium hydroxide, lithium hydroxide, potassium hydroxide and tris.

Prodrugs mean compounds which are metabolized in vivo to compounds of the general formula I. Typical prodrugs are phosphates, carbamates of amino acids, esters and others.

The novel heterocyclic compounds I can be prepared in various ways.

The possible methods of synthesis are essentially already known or are based on analogous routes which are known. An exemplary method is detailed in synthesis scheme 1.

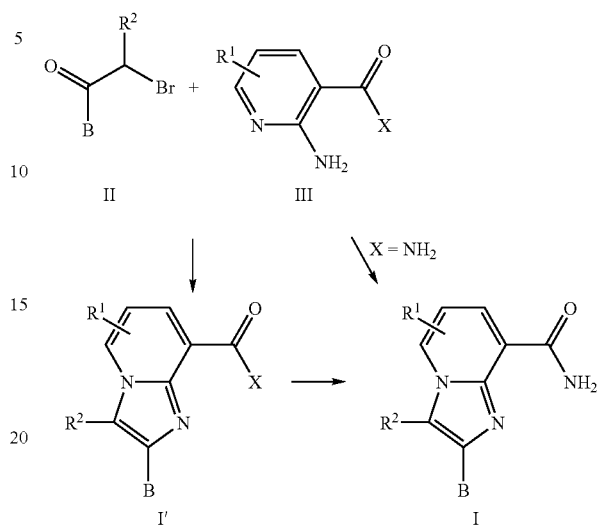

Synthesis scheme 1

An α-bromo ketone II and a 2-aminopyridine derivative III are reacted to give an imidazopyridine I'. This is preferably carried out in polar solvents such as acetone or alcohols, where appropriate with the addition of acids such as hydrobromic acid, and initially at room temperature and later at elevated temperature, for example up to the boiling point of the solvent employed. An alternative possibility is also to operate directly at elevated temperature. If X in III is an $NH_2$ group, the novel compounds I are obtained by the above route. If, on the other hand, X is an ester group such as $OCH_2CH_3$, I' (X=$OCH_2CH_3$) is then converted into I. This can be achieved in two ways.

I' (X=$OCH_2CH_3$) is hydrolyzed to a carboxylic acid I' (X=COOH) in mixtures of polar solvents such as tetrahydrofuran and water or in water directly with the addition of acids such as hydrochloric acid or bases such as sodium hydroxide solution or lithium hydroxide at room temperature or at elevated temperatures, not above the boiling point of the solvent. This carboxylic acid I' (X=COOH) can then be converted into the carboxamide with ammoniacal solutions, for example $NH_3$ in alcohols or water, in organic solvents, preferably in polar, aprotic solvents such as tetrahydrofuran and dimethylformamide, using conventional peptide coupling methods, which, as shown in scheme 1, represents the novel compounds I. Some peptide coupling methods are listed, for example, in Houben-Weyl, Methoden der Organischen Chemie, $4^{th}$ ed., E5, chap. V and R. C. Larock, Comprehensive Organic Transformations, VCH Publisher, 1989, pages 972 et seq.

Otherwise, if X in I' is O-alkyl, this ester can be converted directly with ammonia, where appropriate at elevated temperature and under elevated pressure, into the novel amide I. Alternatively, the ester I' (X=O-alkyl) can be reacted with hydrazine in polar solvents such as the alcohols butanol and ethanol or else dimethyl formamide, at elevated temperatures, preferably 80 to 130° C., resulting in a hydrazide I' (X=$NHNH_2$) which can then be reduced under reductive conditions, such as with Raney nickel in alcohols under reflux, to the novel amide I.

The substituted heterocyclic compounds I obtained in the present invention are inhibitors of the enzyme poly(ADP-ribose)polymerase or PARP (EC 2.4.2.30).

The inhibitory effect of the substituted heterocyclic compounds I has been measured using an enzyme assay disclosed in the literature, measuring a $K_i$ as criterion of the effect. The heterocyclic compounds I were measured in this way for an inhibitory effect on the enzyme poly(ADP-ribose)polymerase or PARP (EC 2.4.2.30).

The substituted heterocyclic compounds of the general formula I are inhibitors of poly(ADP-ribose)polymerase (PARP) or, as it is also called, poly(ADP-ribose)synthase (PARS), and can thus be used for the treatment and prophylaxis of disorders which are associated with an enzymatic activity of these enzymes which is elevated and/or to be reduced.

The compounds of the formula I can be employed for producing drugs for the treatment of damage after ischemias and for prophylaxis when ischemias are expected in various organs.

The present heterocyclic compounds of the general formula I can accordingly be used for the treatment and prophylaxis of neurodegenerative disorders occurring after ischemia, trauma (craniocerebral trauma), massive bleeding, subarachnoid hemorrhages and stroke, and of neurodegenerative disorders such as multi-infarct dementia, Alzheimer's disease, Huntington's diseases and of epilepsies, especially of generalized epileptic seizures such as, for example, petit mal and tonoclonic seizures and partial epileptic seizures such as temporal lobe, and complex partial seizures, and further for the treatment and prophylaxis of damage to the heart after cardiac ischemias and damage to the kidneys after renal ischemias, for example of acute renal insufficiency caused by drug therapies such as in cyclosporin treatment, of acute kidney failure or of damage occurring during and after a kidney transplant. The compounds of the general formula I can also be used for treating acute myocardial infarction and damage occurring during and after medical lysis thereof (for example with TPA, reteplase, streptokinase or mechanically with a laser or Rotablator) and of microinfarets during and after heart valve replacement, aneurysm resections and heart transplants. The present imidazopyridine derivatives I can likewise be used for treatment for revascularization of critically narrowed coronary arteries, for example in PTCA and bypass operations, and critically narrowed peripheral arteries, for example leg arteries. The heterocyclic compounds I can additionally be beneficial in the chemotherapy of tumors and metastasis thereof and be used for treating inflammations and rheumatic disorders such as, for example, rheumatoid arthritis and also for treating diabetes mellitus and for treating multiorgan failure, for example associated with septic shock, and for treating ARDS (acute respiratory distress syndrome, shock lung).

The novel pharmaceutical preparations comprise a therapeutically effective amount of the compounds I in addition to conventional pharmaceutical excipients.

For local external use, for example in dusting powders, ointments or sprays, the active ingredients can be present in the usual concentrations. The active ingredients are ordinarily present in an amount of from 0.001 to 1% by weight, preferably 0.001 to 0.1% by weight.

On internal use, the preparations are administered in single doses. From 0.1 to 100 mg are given per kg of body weight in a single dose. The preparations can be administered in one or more doses each day depending on the nature and severity of the disorders.

Appropriate for the required mode of administration, the novel pharmaceutical preparations contain conventional carriers and diluents in addition to the active ingredient. It is possible for local external use to use pharmaceutical excipients such as ethanol, isopropanol, ethoxylated castor oil, ethoxylated hydrogenated castor oil, polyacrylic acid, polyethylene glycol, polyethylene glycol stearate, ethoxylated fatty alcohols, liquid paraffin, petrolatum and wool fat. Suitable for internal use are, for example, lactose, propylene glycol, ethanol, starch, talc and polyvinylpyrrolidone.

It is also possible for antioxidants such as tocopherol and butylated hydroxyanisole, and butylated hydroxytoluene, flavor-improving additives, stabilizers, emulsifiers and lubricants to be present.

The substances present in the preparation in addition to the active ingredient, and the substances used for producing the pharmaceutical preparations, are toxicologically acceptable and compatible with the particular active ingredient. The pharmaceutical preparations are produced in a conventional way, for example by mixing the active ingredient with conventional carriers and diluents.

The pharmaceutical preparations can be administered in various ways, for example orally, parenterally such as intravenously by infusion, subcutaneously, intraperitoneally and topically. Thus, preparation forms such as tablets, emulsions, solutions for infusion and injection, pastes, ointments, gels, creams, lotions, dusting powders and sprays are possible.

EXAMPLE A: Inhibition of the Enzyme Poly(ADP-Ribose)Polymerase or PARP (EC 2.4.2.30)

A 96-well microtiter plate (Falcon) is coated with histones (type II-AS; SIGMA H7755). Histones are for this purpose dissolved in carbonate buffer (0.05 M $NaHCO_3$; pH 9.4) at a concentration of 50 µg/ml. The individual wells of the microtiter plate are each incubated with 100 µl of this histone solution overnight. The histone solution is then removed and the individual wells are incubated with 200 µl of a 1% strength BSA (bovine serum albumin) solution in carbonate buffer at room temperature for 2 hours. They are then washed three times with washing buffer (0.05% Tween10 in PBS). For the enzyme reaction, 50 µl of the enzyme reaction solution (5 µl of reaction buffer (1M Tris-HCl pH 8.0, 100 mM $MgCl_2$, 10 mM DTT), 0.5 µl of PARP (c=0.22 µg/µl), 4 µl of activated DNA (SIGMA D-4522, 1 mg/ml in water), 40.5 µl of $H_2O$) are preincubated in each well with 10 µl of an inhibitor solution for 10 minutes. The enzyme reaction is started by adding 40 µl of a substrate solution (4 µl of reaction buffer (see above), 8 µl of NAD solution (100 µM in $H_2O$), 28 µl of $H_2O$). The reaction time is 20 minutes at room temperature. The reaction is stopped by washing three times with washing buffer (see above). This is followed by incubation with a specific anti-polyADP-ribose antibody at room temperature for one hour. The antibodies used were monoclonal anti-poly(ADP-ribose) antibodies "10H" (Kawamitsu H et al. (1984) Monoclonal antibodies to poly(adenosine diphosphate ribose) recognize different structures. Biochemistry 23, 3771–3777). It is likewise possible to use polyclonal antibodies.

The antibodies were employed in a 1:5000 dilution in antibody buffer (1% BSA in PBS; 0.05% Tween20). Washing with washing buffer three times is followed by incubation with the secondary antibody at room temperature for one hour. The monoclonal antibody used for this was an anti-mouse IgG coupled to peroxidase (Boehringer Mannheim), and the rabbit antibody used for this was an anti-rabbit IgG coupled to peroxidase (SIGMA A-6154), each in a 1:10000 dilution in antibody buffer. Washing with washing buffer three times is followed by the color reaction using 100 μl/well of color reagent (SIGMA, TMB mix, T8540) at room temperature for about 15 min. The color reaction is stopped by adding 100 μl of 2M $H_2SO_4$. Measurement is then carried out immediately (450 nm versus 620 nm; ELISA plate reader EAR340AT "Easy Reader", SLT-Labinstruments, Austria). The $IC_{50}$ of an inhibitor to be measured is the concentration of inhibitor where a half-maximum change in color concentration occurs.

Test of PARP Inhibitors in the Cellular Assay

To test the effect of PARP inhibitors, eukaryotic cell lines are treated with chemicals so that the DNA of the cell line is damaged and thus the PARP enzyme present in the cells is activated. Activation of the enzyme results in formation of chains of polyADP-ribose (PAR) on proteins. These chains are bound by a specific antibody. The latter is in turn bound by a second antibody which is provided with a fluorescent label. The fluorescence is measured with a fluorescence scanner and the behaves proportionally to the activity of the enzyme PARP. PARP inhibitors can be recognized by a diminution of the fluorescence signal. In order to avoid falsification of the results by different numbers of cells, the DNA of the cells is labeled with another dye and its fluorescence is likewise determined in the fluorescence scanner.

400,000 cells of the human cell line C4I are incubated in RPMI medium with 10% fetal calf serum in cell culture plates with 24 wells at 37° C., 5% $CO_2$ until a dense cell lawn is reached. The cells are washed with DMEM, and the PARP inhibitors to be tested are added in various concentrations in DMEM. After incubation at 37° C. for 20 min, a hydrogen peroxide concentration of 1 mM is set up and incubation is continued at 37° C. for 10 min. As a check, cells in some wells are not treated with hydrogen peroxide (no PARP activation) or receive no inhibitor (maximum PARP activation). The cells are fixed for 10 min at −20° C. by adding methanol/acetone mixture (7 parts of methanol, 3 parts of acetone) which has previously been cooled to −20° C. The cells are then dried and rehydrated by adding PBS at room temperature for 10 min, and nonspecific binding sites are blocked in PBS with 0.05% Tween20 and 5% dry milk powder at room temperature for 30 min. The mouse anti-PAR antibody is added in a concentration of 20 μg/ml in PBS with 0.05% Tween20 and 5% dry milk powder and incubated at 37° C. for 1 h. Unbound antibody is removed by washing five times with PBS for 5 min each time. This is followed by incubation with a diluted goat anti-mouse FITC-coupled second antibody (dilution 1:50 in PBS with 0.05% Tween20, 5% dry milk powder and 1 μg/ml DAPI (4',6-diamidino-2-phenylindole) at 37° C. for 30 min. Unbound antibody is removed by washing five times with PBS for 5 min each time. The FITC and DAPI fluorescences are measured at several sites in the wells using a fluorescence scanner. Ths FITC signal and the DAPI signal are standardized for the evaluation. The $IC_{50}$ values are calculated by semilogarithmic plotting of the standardized values of the various inhibitor concentrations.

EXAMPLES

Example 1

2-Phenylimidazo[1,2-a]pyridine-8-carboxamide a) Ethyl 2-phenylimidazo[1,2-a]pyridine-8-carboxylate x HBr 2.0 g (12 mmol) of ethyl 2-aminonicotinate and 2.4 g (12 mmol) of 2'-bromoacetophenone were mixed with 100 ml of acetone and stirred at room temperature for 16 hours. The mixture was then refluxed for 3 hours. After cooling, the mixture was concentrated in vacuo. The residue was stirred into 100 ml of methanol and then 1 ml of 47% strength hydrobromic acid in glacial acetic acid was cautiously added. The mixture was refluxed for one hour and then again concentrated in vacuo. This residue was dissolved in the minimum amount of methanol, and 3 ml of 47% strength hydrobromic acid were added. Ether was then added cautiously to incipient turbidity, after which the product slowly crystallized. 2.5 g were obtained.

b) 2-Phenylimidazo[1,2-a]pyridine-8-carboxylic acid 1.9 g (5.5 mmol) of the intermediate 1a were dissolved in 50 ml of methanol. After addition of 70 ml of 4M sodium hydroxide solution, the mixture was refluxed for two hours. After cooling, the organic solvent was removed in vacuo. The resulting precipitate was filtered off with suction and dissolved in hot water. This solution was cautiously neutralized with dilute hydrochloric acid and cooled overnight. The product precipitated during this. 0.71 g was obtained.

c) 2-Phenylimidazo[1,2-a]pyridine-8-carboxamide 0.7 g (2.9 mmol) of the intermediate 1b and 0.4 g (2.9 mmol) of 1-hydroxy-1H-benzotriazole x hydrate were dissolved in 40 ml of anhydrous dimethylformamide, and 150 ml of a 0.5 M ammonia solution in dioxane were added. Then, at 10° C., 0.56 g (2.9 mmol) of N'-(3-dimethylaminopropyl)-N-ethylcarbodiimide was added, and the mixture was stirred at room temperature for 16 hours. This reaction solution was concentrated in vacuo. The residue was then partitioned between aqueous sodium bicarbonate solution and ethyl acetate. The organic phase was separated off, washed once more with water, dried and concentrated in vacuo. The residue obtained in this way was treated with a little methylene chloride, whereupon the product crystallized. 0.25 g of product was obtained.

$^1$H-NMR ($D_6$-DMSO): δ=7.1 (H), 7.35(1H), 7.5(2H), 8.0(4H), 8.6(1H), 8.8(1H) and 9.7(1H)ppm.

Example 2

2-(4-Nitrophenyl)imidazo[1,2-a]pyridine-8-carboxamide

The product was prepared in analogy to Example 1 from ethyl 2-aminonicotinate and 2'-bromo-4-nitroacetophenone.

$^1$H-NMR ($D_6$-DMSO): δ=7.1(1H), 8.1(1H), 8.2(1H), 8.3 (4H), 8.8(2H) and 9.5(1H) ppm.

Example 3

2-(4-Aminophenyl)imidazo[1,2-a]pyridine-8-carboxamide

The product from Example 2 was dissolved in alcohol and, after addition of palladium/carbon, hydrogenated with hydrogen. This was followed by filtration and concentration of the filtrate in vacuo. The product was obtained.

¹H-NMR (D₆-DMSO): δ=5.35(2H), 6.7(2H), 7.0(1H), 7.7(2H), 7.9(2H), 8.2(1H), 8.7(1H) and 9.8(1H) ppm.

Example 4

2-(2-Benzothienyl)imidazo[1,2-a]pyridine-8-carboxamide

The product was prepared in analogy to the method of Example 1 using benzothiophene-2-carboxaldehyde.

¹H-NMR (D₆-DMSO): δ=7.1(1H), 7.5(2H), 8.1(3H), 8.4(1H), 8.5(1H), 8.7(1H), 8.8(1H) and 9.6(1H) ppm.

Example 5

2-(4-Bromophenyl)-imidazo[1,2-a]pyridine-8-carboxamide

The product was prepared in analogy to Example 1 from ethyl 2-aminonicotinate and 2',4-dibromoacetophenone.

¹H-NMR (D₆-DMSO): δ=7.1(1H), 7.7(2H), 7.9–8.1(3H), 8.1(1H, broad), 8.6(1H), 8.75(1H), 9.55(1H, broad).

Example 6

2-(4-Imidazol-1-ylphenyl)imidazo[1,2-a]pyridine-8-carboxamide

The product was prepared in analogy to Example 1 from ethyl 2-aminonicotinate and 2'-bromo-4-(imidazol-1-yl)acetophenone.

¹H-NMR (D₆-DMSO): δ=7.0–7.2(2H), 7.75–7.95(3H), 8.05(2H), 8.1(2H), 8.25(1H), 8.7(1H), 8.8(1H), 9.6(1H).

The following novel compounds can be prepared in analogy to the methods described above:

1. 2-(4-(4-n-propyl-piperazin-1-yl)-phenyl)-imidazo[1,2-a]pyridine-8-carboxamide
2. 2-(4-piperazin-1-yl-phenyl)-imidazo[1,2-a]pyridine-8-carboxamide
3. 2-(4-(4-isopropyl-piperazin-1-yl)-phenyl)-imidazo[1,2-a]pyridine-8-carboxamide
4. 2-(4-(4-benzyl-piperazin-1-yl)-phenyl)-imidazo[1,2-a]pyridine-8-carboxamide
5. 2-(4-(4-n-butyl-piperazin-1-yl)-phenyl)-imidazo[1,2-a]pyridine-8-carboxamide
6. 2-(4-(4-ethyl-piperazin-1-yl)-phenyl)-imidazo[1,2-a]pyridine-8-carboxamide
7. 2-(4-(2-N,N-dimethylamino-eth-1-yloxy)-phenyl)-imidazo-[1,2-a]pyridine-8-carboxamide
8. 2-(4-(2-pyrrolidin-1-yl-eth-1-yloxy)-phenyl)-imidazo[1,2-a]pyridine-8-carboxamide
9. 2-(4-(2-piperidin-1-yl-eth-1-yloxy)-phenyl)-imidazo[1,2-a]pyridine-8-carboxamide
10. 2-(4-(2-piperazin-1-yl-eth-1-yloxy)-phenyl)-imidazo[1,2-a]pyridine-8-carboxamide
11. 2-(4-(2-(4-methyl-piperazin-1-yl)-eth-1-yloxy)-phenyl)-imidazo[1,2-a]pyridine-8-carboxamide
12. 2-(4-(2-(4-propyl-piperazin-1-yl)-eth-1-yloxy)-phenyl)-imidazo[1,2-a]pyridine-8-carboxamide
13. 2-(4-(2-(4-ethyl-piperazin-1-yl)-eth-1-yloxy)-phenyl)-imidazo[1,2-a]pyridine-8-carboxamide
14. 2-(4-(2-(4-benzyl-piperazin-1-yl)-eth-1-yloxy)-phenyl)-imidazo[1,2-a]pyridine-8-carboxamide
15. 2-(4-(2-(4-acetamido-piperazin-1-yl)-eth-1-yloxy)-phenyl-imidazo[1,2-a]pyridine-8-carboxamide
16. 2-(4-(2-(4-benzamido-piperazin-1-yl)-eth-1-yloxy)-phenyl-imidazo[1,2-a]pyridine-8-carboxamide
17. 2-(4-homopiperazin-1-yl-phenyl)-imidazo[1,2-a]pyridine-8-carboxamide
18. 2-(4(4-methylhomopiperazin-1-yl)-phenyl)-imidazo[1,2-a]pyridine-8-carboxamide
19. 2-(4(4-benzylhomopiperazin-1-yl)-phenyl)-imidazo[1,2-a]pyridine-8-carboxamide
20. 2-(4-(4-n-butyl-homopiperazin-1-yl)-phenyl)-imidazo[1,2-a]pyridine-8-carboxamide
21. 2-(4(4-ethylhomo-piperazin-1-yl)-phenyl)-imidazo[1,2-a]pyridine-8-carboxamide
22. 2-(4-methoxy-phenyl)-imidazo[1,2-a]pyridine-8-carboxamide
23. 2-(4-methyl-phenyl)-imidazo[1,2-a]pyridine-8-carboxamide
24. 2-(4-phenyl-phenyl)-imidazo[1,2-a]pyridine-8-carboxamide
25. 2-(4-isopropyl-phenyl)-imidazo[1,2-a]pyridine-8-carboxamide
26. 2-(4-fluoro-phenyl)-imidazo[1,2-a]pyridine-8-carboxamide
27. 2-(4-trifluoromethyl-phenyl)-imidazo[1,2-a]pyridine-8-carboxamide
28. 2-(3-methoxy-phenyl)-imidazo[1,2-a]pyridine-8-carboxamide
29. 2-(3-chloro-phenyl)-imidazo[1,2-a]pyridine-8-carboxamide
30. 2-(3-amino-phenyl)-imidazo[1,2-a]pyridine-8-carboxamide
31. 2-(3-methyl-phenyl)-imidazo[1,2-a]pyridine-8-carboxamide
32. 2-(3-phenyl-phenyl)-imidazo[1,2-a]pyridine-8-carboxamide
33. 2-(3-isopropyl-phenyl)-imidazo[1,2-a]pyridine-8-carboxamide
34. 2-(3-fluoro-phenyl)-imidazo[1,2-a]pyridine-8-carboxamide
35. 2-(3-trifluoromethyl-phenyl)-imidazo[1,2-a]pyridine-8-carboxamide
36. 2-pipetidin-4-yl-imidazo[1,2-a]pyridine-8-carboxamide
37. 2-(1-methyl-piperidin-4-yl)-imidazo[1,2-a]pyridine-8-carboxamide
38. 2-(1-ethyl-piperidin-4-yl)-imidazo[1,2-a]pyridine-8-carboxamide
39. 2-(1-n-propyl-piperidin-4-yl)-imidazo[1,2-a]pyridine-8-carboxamide
40. 2-(1-benzyl-piperidin-4-yl)-imidazo[1,2-a]pyridine-8-carboxamide
41. 2-(1-n-butyl-piperidin-4-yl)-imidazo[1,2-a]pyridine-8-carboxamide
42. 2-(1-isopropyl-piperidin-4-yl)-imidazo[1,2-a]pyridine-8-carboxamide
43. 2-pyridin-4-yl-imidazo[1,2-a]pyridine-8-carboxamide
44. 2-pyridin-3-yl-imidazo[1,2-a]pyridine-8-carboxamide
45. 2-pyridin-2-yl-imidazo[1,2-a]pyridine-8-carboxamide
46. 2-thien-2-yl-imidazo[1,2-a]pyridine-8-carboxamide
47. 2-thien-3-yl-imidazo[1,2-a]pyridine-8-carboxamide
48. 2-indol-3-yl-imidazo[1,2-a]pyridine-8-carboxamide
49. 2-indol-5-yl-imidazo[1,2-a]pyridine-8-carboxamide
50. 2-indol-2-yl-imidazo[1,2-a]pyridine-8-carboxamide
51. 2-quinolin-3-yl-imidazo[1,2-a]pyridine-8-carboxamide
52. 2-quinolin-2-yl-imidazo[1,2-a]pyridine-8-carboxamide
53. 2-quinolin-4-yl-imidazo[1,2-a]pyridine-8-carboxamide
54. 2-isoquinolin-1-yl-imidazo[1,2-a]pyridine-8-carboxamide
55. 2-isoquinolin-3-yl-imidazo[1,2-a]pyridine-8-carboxamide
56. 2-quinoxalin-2-yl-imidazo[1,2-a]pyridine-8-carboxamide
57. 2-naphth-2-yl-imidazo[1,2-a]pyridine-8-carboxamide 58. 2-naphth-1-yl-imidazo[1,2-a]pyridine-8-carboxamide
59. 2-(4-(2(N,N-dimethylamino)-eth-1-ylamino)-phenyl)-imidazo[1,2-a]pyridine-8-carboxamide
60. 2-(4-(2(N,N-diethylamino)-eth-1-ylamino)-phenyl)-imidazo[1,2-a]pyridine-8-carboxamide
61. 2-(4-(2-piperidin-1-yl-eth-1-ylamino)-phenyl)-imidazo[1,2-a]pyridine-8-carboxamide
62. 2-(4-(2-pyrrolidin-1-yl-eth-1-ylamino)-phenyl)-imidazo[1,2-a]pyridine-8-carboxamide
63. 2-(4-(3(N,N-dimethylamino)-prop-1-ylamino)-phenyl)-imidazo[1,2-a]pyridine-8-carboxamide
64. 2-(4-(3(N,N-diethylamino)-prop-1-ylamino)-phenyl)-imidazo[1,2-a]pyridine-8-carboxamide
65. 2-(4-(3-piperidin-1-yl-prop-1-ylamino)-phenyl)-imidazo[1,2-a]pyridine-8-carboxamide
66. 2-(4-(3-pyrrolidin-1-yl-prop-1-ylamino)-phenyl)-imidazo-[1,2-a]pyridine-8-carboxamide
67. 2-cyclohexyl-imidazo[1,2-a]pyridine-8-carboxamide
68. 2-(cis-4-amino-cyclohex-1-yl)-imidazo[1,2-a]pyridine-8-carboxamide
69. 2-(4-methoxy-cyclohex-1-yl)-imidazo[1,2-a]pyridine-8-carboxamide
70. 2-(4-(2(N,N-dimethylamino)-eth-1-yl-methylamino)-phenyl)-imidazo[1,2-a]-pyridine-8-carboxamide
71. 2-(4-(4-methyl-piperazin-1-yl)-phenyl)-imidazo[1,2-a]pyridine-8-carboxamide

We claim:
1. Compound of the formula I

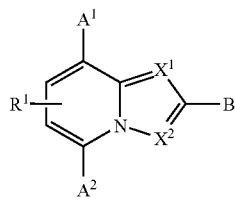

(I)

in which
A$^1$ is carboxamide, and
A$^2$ is hydrogen, and
X$^1$ is N or C—R$^2$, and
X$^2$ is CH, and
R$^2$ is hydrogen, C$_1$–C$_6$-alkyl, C$_1$–C$_4$-alkyl-phenyl, or phenyl and
R$^1$ is hydrogen, and
B is optionally substituted thienyl, pyridinyl, indolyl, quinolinyl, isoquinolinyl, piperidinyl, cyclohexyl, naphthyl, quinoxalinyl, phenyl or phenyl further substituted with piperazinyl, piperidinyl or pyrrolidinyl; each of which is optionally substituted by one R$^4$ and a maximum of three identical or different R$^5$ radicals, and
R$^4$ is hydrogen or -(D)$_p$-(E)$_s$-(F$^1$)$_q$-G$^1$-(F$^2$)$_r$-(G$^2$)-G$^3$, where
D is S, NR$^{43}$ or O
E is -phenyl,

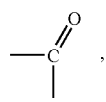

—SO$_2$—, —SO$_2$NH—, NHCO—, —CONH, or —NHSO$_2$, and
s is 0 or 1 and
G$^1$ is a bond or an unsaturated, saturated or partially unsaturated mono-, bi- or tricyclic ring with a maximum of 15 carbon atoms, or an unsaturated, saturated or partially saturated mono-, bi- or tricyclic ring with a maximum of 14 carbon atoms and 0 to 5 nitrogen atoms, 0 to 2 oxygen atoms and 0 to 2 sulfur atoms, each of which is also substituted by a maximum of 3 different or identical R$^5$ radicals, and one or two carbon or sulfur atoms may also carry one or two =O groups, and
G$^2$ is NR$^{41}$R$^{42}$,

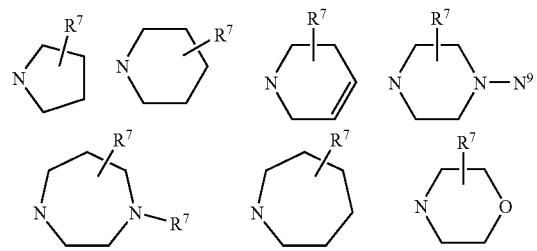

or a bond and
G$^3$ is an unsaturated, saturated or partially unsaturated mono-, bi- or tricyclic ring with a maximum of 15 carbon atoms, or an unsaturated, saturated or partially unsaturated mono-, bi- or tricyclic ring with a maximum of 14 carbon atoms and 0 to 5 nitrogen atoms, 0 to 2 oxygen atoms and 0 to 2 sulfur atoms, each of which is also substituted by a maximum of 3 different or identical R$^5$ radicals, and one or two carbon or sulfur atoms may also carry one or two =O groups, or is hydrogen, and
p is 0 or 1 and
F$^1$ is a C$_1$–C$_8$-alkyl chain, and
F$^2$ independently of F$^1$ has the same meaning as F$^1$,
q is 0 or 1, and
r is 0 or 1 and
R$^{41}$ is hydrogen, C$_1$–C$_6$-alkyl, C$_1$–C$_6$-alkyl-phenyl, phenyl, it being possible for each carbon atom of the alkyl chains and the phenyl rings also to carry a maximum of two R$^6$ radicals, or (CH$_2$)$_t$—K and
R$^{42}$ is hydrogen, C$_1$–C$_6$-alkyl, —CO$_2$—R$^8$, —CO—R$^8$, —SO$_2$—R$^8$, —(C=NH)—R$^8$ or —(C=NH)—NHR$^8$ and
is hydrogen or C$_1$–C$_4$-alkyl and
t is 1, 2, 3, or 4 and
K is NR$^{11}$R$^{12}$, NR$^{11}$—C$_1$–C$_4$-alkyl-phenyl, pyrrolidine, piperidine, 1,2,5,6-tetrahydropyridine, morpholine, homopiperidine, homopiperazine, or piperazine, each of which is optionally substituted by a C$_1$–C$_6$-alkyl radical or also by a C$_1$–C$_6$-alkyl-phenyl radical and the phenyl radical can also be substituted by a maximum of two R$^{81}$,
R$^5$ is hydrogen, chlorine, fluorine, bromine, iodine, C$_1$–C$_6$-alkyl, nitro, CF$_3$, CN, NR$^{11}$R$^{12}$, NH—CO—R$^{13}$, or O—C$_1$–C$_4$-alkyl, and
R$^6$ is hydrogen, chlorine, fluorine, bromine, iodine, C$_1$–C$_6$-alkyl, OH, nitro, CF$_3$, CN, NR$^{11}$R$^{12}$, NH—CO—R$^{13}$, or O—C$_1$–C$_4$-alkyl, and
R$^7$ is hydrogen, C$_1$–C$_6$-alkyl, phenyl, optionally substituted by up to two identical or different R$^{71}$ radicals, or an amine $NR^{11}R^{12}$, or a cyclic saturated amine with 3 to 7 members, which may also be substituted by an alkyl radical $C_1$–$C_6$-alkyl, $R^{11}$ and $R^{12}$ are, independently of one another, hydrogen or $C_1$–$C_4$-alkyl, and $R^{13}$ is hydrogen, $C_1$–$C_4$-alkyl, $C_1$–$C_4$-alkyl-phenyl or phenyl, and $R^{71}$ is OH, $C_1$–$C_6$-alkyl, O—$C_1$–$C_4$-alkyl, chlorine, bromine, iodine, fluorine, $CF_3$, nitro or $NH_2$, and $R^8$ is $C_1$–$C_6$-alkyl, $CF_3$, phenyl or $C_1$–$C_4$-alkyl-phenyl, where the phenyl ring is optionally substituted by up to two $R^{81}$ radicals, and $R^{81}$ is OH, $C_1$–$C_6$-alkyl, O—$C_1$–$C_4$-alkyl, chlorine, bromine, iodine, fluorine, $CF_3$, nitro or $NH_2$, and $R^9$ is hydrogen, $C_1$–$C_6$-alkyl, $C_1$–$C_4$-alkyl-phenyl, $CO_2$—$C_1$–$C_4$-alkyl-phenyl, $CO_2$—$C_1$–$C_4$-alkyl, —$SO_2$-phenyl, —$COR^8$ or phenyl, where the phenyl rings are optionally substituted by up to two identical or different $R^{91}$ radicals, and $R^{91}$ is OH, $C_1$–$C_6$-alkyl, O—$C_1$–$C_6$-alkyl, chlorine, bromine, iodine, fluorine, $CF_3$, nitro or $NH_2$, or the tautomeric forms, possible enantiomeric and diastereomeric forms thereof.

2. A compound of the formula I as claimed in claim 1, where

B is phenyl, pyridine or piperidine, each of which may also be substituted by an $R^4$ and $R^5$ radical.

3. A compound of the formula I as claimed in claim 1, where $R^4$ is hydrogen or $D_{0,1}$-$F^1_{0,1}$-$G^2$-$G^3$ where $G^3$ is hydrogen and $G^2$ is not a bond and D is O or $NR^{43}$, where $R^{43}$ is hydrogen or $C_1$–$C_3$-alkyl and $F^1$ is $C_2$–$C_4$-alkyl.

4. A process for the treatment or prophylaxis of damage due to an ischemia, said process comprising administering an effective amount of a drug produced from the compound of claim 1 to a patient in need thereof.

5. A process for the treatment of damage to the heart after a cardiac ischemia, said process comprising administering an effective amount of a drug produced from the compound of claim 1 to a patient suffering from said damage.

6. A drug comprising a compound of claim 1 and a pharmaceutically acceptable carrier.

* * * * *

UNITED STATES PATENT AND TRADEMARK OFFICE
CERTIFICATE OF CORRECTION

PATENT NO. : 7,041,675 B2 Page 1 of 1
APPLICATION NO. : 10/182532
DATED : May 9, 2006
INVENTOR(S) : Wilfried Lubisch et al.

It is certified that error appears in the above-identified patent and that said Letters Patent is hereby corrected as shown below:

Column 12, line 37, No. 36 should be corrected to read --2-piperidin-4-yl-- instead of "2-pipetidin-4-yl";

Column 14, line 20, Claim 1, 4th figure should be corrected to show

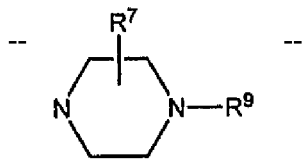

instead of

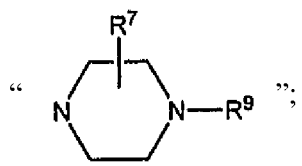

Column 14, line 51 should be corrected to read --$R^{43}$ is hydrogen or $C_1$-$C_4$-alkyl and--.

Signed and Sealed this

Twenty-eighth Day of August, 2007

JON W. DUDAS
*Director of the United States Patent and Trademark Office*